(12) United States Patent
Ataullakhanov et al.

(10) Patent No.: US 10,342,842 B2
(45) Date of Patent: Jul. 9, 2019

(54) PHARMACEUTICAL COMPOSITIONS HAVING ANTIBACTERIAL, ANTIVIRAL, AND OTHER IMMUNOSTIMULATORY ACTIVITIES

(71) Applicant: 9541659 CANADA INC., Toronto (CA)

(72) Inventors: Ravshan I. Ataullakhanov, Moscow (RU); Aleksey V. Pichugin, Moscow (RU); Tatyana M. Melnikova, Moscow (RU); Rakhim M. Khaitov, Moscow (RU)

(73) Assignee: 9541659 Canada Inc., Toronto (CA)

( * ) Notice: Subject to any disclaimer, the term of this patent is extended or adjusted under 35 U.S.C. 154(b) by 104 days.

(21) Appl. No.: 15/160,381

(22) Filed: May 20, 2016

(65) Prior Publication Data

US 2016/0263175 A1 Sep. 15, 2016

Related U.S. Application Data

(63) Continuation of application No. PCT/RU2014/000541, filed on Jul. 22, 2014.

(30) Foreign Application Priority Data

Nov. 21, 2013 (RU) .................................. 2013151824

(51) Int. Cl.
| | |
|---|---|
| A61K 36/81 | (2006.01) |
| A61K 38/02 | (2006.01) |
| A01N 65/38 | (2009.01) |
| A61K 31/715 | (2006.01) |
| B01D 11/02 | (2006.01) |
| A61K 38/00 | (2006.01) |

(52) U.S. Cl.
CPC .............. *A61K 36/81* (2013.01); *A01N 65/38* (2013.01); *A61K 31/715* (2013.01); *A61K 38/02* (2013.01); *A61K 38/00* (2013.01); *A61K 2236/15* (2013.01); *A61K 2236/331* (2013.01); *A61K 2236/50* (2013.01); *A61K 2236/51* (2013.01); *A61K 2236/53* (2013.01); *B01D 11/02* (2013.01)

(58) Field of Classification Search
CPC .... A61K 36/81; A61K 38/02; A61K 2236/15; A61K 2236/331; A61K 2236/53; A61K 2236/51; A61K 2236/50; A01N 65/38
USPC .................................................... 424/278.1
See application file for complete search history.

(56) References Cited

U.S. PATENT DOCUMENTS

2005/0042236 A1* 2/2005 Ataullakhonov ...... A61K 36/68
424/278.1

FOREIGN PATENT DOCUMENTS

| KR | 20010029185 A | 4/2001 |
|---|---|---|
| RU | 2028303 C1 | 2/1995 |
| RU | 2149642 C1 | 5/2000 |
| RU | 2195308 C1 | 12/2002 |
| RU | 2378015 C2 | 1/2010 |

OTHER PUBLICATIONS

Jameel et al. Design of a Formulation for Freeze Drying. Formulation and Process Development Strategies for Manufacturing Biopharmaceuticals, edited by Jameel and Hershenson. p. 359-492, 2010 John Wiley & Sons, Inc. (Year: 2010).*
International Search Report from International Application No. PCT/RU2014/000541, filed Jul. 22, 2014, dated Mar. 26, 2015.
Patwardhan, B. et al, Botanical immunedrugs: scope and opportunities, Reviews, Drug Discovery Today, Apr. 2005, pp. 495-502, v. 10, No. 7.
Banchereau, J. et al, Dendritic cells and the control of immunity, Nature, Mar. 19, 1998, pp. 245-252, vol. 392.
Usov, A. I., et al, Polysaccharides of Algae 48. Polysaccharide Composition of Several Calcareous Red Algae: Isolation of Alginate from *Corallina pilulifera* P. et R. (Rhodophyta, Corallinaceae), Botanica Marina, 1995, pp. 43-51, vol. 38.
Lowry, O. H., et al., Protein Measurement with the Folin Phenol Reagent, The Journal of Biological Chemistry, May 28, 1951, pp. 265-275.
van Heijenoort, Jean, Formation of the glycan chains in the synthesis of bacterial peptidoglycan, Glycobiology, 2001, pp. 25R-36R, vol. 11, No. 3.
The Bacterial Cell Envelope. The chemical structure of peptidoglycan, Dec. 9, 2013, URL: http://cronodon.com/BioTech/Bacteria_envelope.html.
Schepetkin, I. A., et al, Botanical polysaccharides: marcophage immunomodulation and therapeutic potential, Int. Immunopharmacol. 2006, pp. 317-333, vol. 6.

(Continued)

*Primary Examiner* — Yih-Horng Shiao
(74) *Attorney, Agent, or Firm* — Clark & Elbing LLP

(57) ABSTRACT

A method of producing a substance with antimicrobial, antiviral, and immunostimulatory activities, particularly towards dendritic cells is proposed, provides for using the chopped potato sprouts as plant raw materials are extracted with water, then the aqueous extract is centrifuged, a salt agent is added, and the obtained saline solution is then concentrated using ultrafiltration through a 300-kD filter, then the solution is frozen for 24 hours, thawed, and filtered, and the pellet thus obtained is removed, and the raw peptidoglycan is precipitated from the solution by using an acidic salt agent and is further re-solubilized with alkali, then the alkaline solution is dialyzed against distilled water on a 12 kD filter, and the peptidoglycan having a molecular weight of 500 kD to 17000 kD is purified from the resulting solution using gel permeation chromatography.

6 Claims, 8 Drawing Sheets

(56) References Cited

OTHER PUBLICATIONS

Howard, C. J., et al, The role of dendritic cells in shaping the immune response, Animal Health Research Reviews, 2004, pp. 191-195, v. 5, No. 2.

Mohty, M., et al, Regulation of Dendritic Cell Function with Immunomodulatory Drugs, Current Medicinal Chemistry, Anti-Inflammatory & Anti-Allergy Agents, 2005, pp. 169-175, vol. 4, No. 2.

York, W. S., et al, Isolation and Characterization of Plant Cell Walls and Cell Wall Components, Methods in Enzymology, 1985, pp. 3-40, vol. 118.

Bock, K. et al, Carbon-13 Nuclear Magnetic Resonance Data for Oligosaccharides, Advances in Carbohydrate Chemistry and Biochemistry, 1984, pp. 193-225, vol. 42.

Green, L C., et al, Analysis of Nitrate, Nitrite, and [15N]Nitrate in Biological Fluids, Analytical Biochemistry, 1982, pp. 131-138, vol. 126.

Vollmer W., et al, Peptidoglycan structure and architecture, FEMS Microbiological Review, 2008, pp. 149-167, vol. 32.

\* cited by examiner

PHARMACEUTICAL COMPOSITIONS HAVING ANTIBACTERIAL, ANTIVIRAL, AND OTHER IMMUNOSTIMULATORY ACTIVITIES

RELATED APPLICATIONS

This application is a Continuation Application of International Application PCT/RU2014/000541, filed on Jul. 22, 2014, which in turn claims priority to Russian Patent Applications No. RU2013151824, filed Nov. 21, 2013, both of which are incorporated herein by reference in their entirety.

FIELD OF THE INVENTION

The present invention relates to the field of medicine and, more specifically, to chemical-pharmaceutical industry, and concerns the method of producing a plant-derived substance with antimicrobial, antiviral, and immunostimulatory activities, particularly towards dendritic cells, the substance produced using the said method, and a pharmaceutical composition comprising the said substance.

BACKGROUND OF THE INVENTION

Many plant polysaccharides exhibit apparent biological activities and are widely used for medicinal purposes [Bhushan Patwardhan and Manish Gautam. Botanical immunodrugs: scope and opportunities. //Reviews. DRUG DISCOVERY TODAY. 2005. Vol. 10. P. 495-502]. Compared to bacterial and synthetic analogues, botanical polysaccharides have no side effects and are of low toxicity, which give them considerable advantages during the development of immunomodulatory, antitumor, and wound healing substances [Schepetkin L. A., Quinn M. T. Botanical polysaccharides: macrophage immunomodulation and therapeutic potential. //Int. Immunopharmacol. 2006. Vol. 6. P. 317-333].

The role of dendritic cells in the immune response was first studied by Ralph Steinman [Jacques Banchereau & Ralph M. Steinman. Dendritic cells and the control of immunity. //Nature, 19 Mar. 1998, Vol. 392: 245-52]. Dendritic cells play a key role in the control of the immune response; they capture foreign antigens and stimulate T cell responses. The vaccination outcome and immune response to infection depend on dendritic cells [Howard C J, Charleston B, Stephens S A, Sopp P, Hope J C. The role of dendritic cells in shaping the immune response. //Anim Health Res Rev, 2004, 5(2):191-5]. Therefore, dendritic cells attract close attention as a target for immunomodulatory agents [Mohty M., Gaugler B, Mami N B, Olive D. Regulation of Dendritic Cell Function with Immunomodulatory Drugs Current Medicinal Chemistry. //Anti-Inflammatory & Anti-Allergy Agents, 2005, Vol. 4, No. 2, pp. 169-175(7)].

There is a known method of producing plant-derived polysaccharides with immunomodulatory activity, which involves treating a plant raw material with a formalin water solution, keeping it in acidified water, and then extracting pectic polysaccharides with an ammonium oxalate water solution, treating the extract in a known way, and freeze-drying the desired product. Freshwater flowering plants, e.g., any type of duckweed (*Lemna* spp.) or previously chopped, fresh aerial parts of higher plants, e.g., bladder campion (*Oberna behen* (L)) are used as plant raw materials (Russian Patent 2149642 C1, A 61 35/78, 27.05.2000). However, the produced pectic substances have very low immunostimulatory activity (the stimulation index for neutrophils and macrophages is 1.09 to 1.12 and 1.12 to 1.39, respectively) and do not have activity towards dendritic cells.

There is a known substance with anti-infective activity and without hemagglutinating activity, which is obtained from dividing cells of plants (corn, potato, mushroom) and is named as Gamma-plant (γ-PL) (L. A. Chekanovskaya, Russian Patent 2028303 C1, C08B37/00). Physical-chemical properties of the biologically active substance Gamma-plant have been described. The latter is a glycoprotein with a molecular weight of 900-2000 kD, consisting of carbohydrate and protein portions with the percent weight ratio of 90:10. At the same time, the carbohydrate portion of the substance comprises 70-80% of glucose and 12-18% of uronic acid.

Disadvantages of the known solution are the mitogenic activity of the substance, which may lead to polyclonal activation of cells, making it dangerous to use the substance as a drug, and the absence of immunostimulatory activity towards dendritic cells and macrophages.

There is also a known method of producing a substance with immunostimulatory, antiviral, and antimicrobial activities, the substance produced using the said method, and a pharmaceutical composition based on the said substance (Russian Patent no. 2195308 A 61K 35/78, 27.12.2002). This method involves extracting the chopped plant raw material with water, centrifuging, concentrating, and precipitating the aqueous extract, and purifying and drying the desired product. Plants of Dioscoreaceae, Plantaginaceae, and Solanaceae families can be used as plant raw materials. Precipitation is performed with 96% ethanol in the presence of sodium chloride. The precipitate is re-precipitated with a salt or acidic agent, and the raw acidic peptidoglycan thus obtained is treated with alkali or a saturated solution of alkali metal salt. The desired product is purified using gel permeation chromatography. The substance produced using this method is a water-soluble acidic peptidoglycan having a molecular weight of 1200-40000 kD and glucose to uronic acid weight ratio of 1 to 2-4. The peptide portion of the molecule of acidic peptidoglycan is 13±3 wt %.

The disadvantage of the known method concerns the difficulty of precipitation (consequent reprecipitation with ethanol). The known substance does not have immunostimulatory activity towards dendritic cells.

SUMMARY OF THE INVENTION

The task of the present invention was to produce a novel plant-derived polysaccharide-based substance from available plant raw materials and with good yield, which is well soluble in water and has not only strong antiviral and antimicrobial activities but also immunostimulatory activity, particularly towards dendritic cells, develop the effective and technological method of producing the said substance, and create a highly effective pharmaceutical composition based on the said substance.

To achieve this task, a method of producing a substance with antimicrobial, antiviral, and immunostimulatory activities, particularly towards dendritic cells has been developed, consisting in that the chopped potato sprouts used as a plant raw material are extracted with water, then the aqueous extract is separated from the pellet, a salt agent is added to the extract, and the resulting saline solution is then concentrated using ultrafiltration through a 300-kD filter, then the solution is frozen for 24 hours, thawed, and filtered, and the pellet thus obtained is removed, and the crude peptidoglycan is precipitated from the solution by using an acidic salt agent and is further re-solubilized with alkali, then the alkaline solution is dialyzed against distilled water on a filter, and the peptidoglycan is purified from the resulting solution using gel permeation chromatography.

In this embodiment, sodium chloride is mainly used as a salt agent, an inorganic ammonium salt is used as an acidic salt agent at the precipitation stage, and the alkaline solution is dialyzed against distilled water on a 12-kD filter.

The produced substance has antimicrobial, antiviral, and immunostimulatory activities, particularly towards dendritic cells, and is a complex biopolymer comprising the polysaccharide, peptide, and lipid portions.

The polysaccharide portion of molecule is 40-60% of the weight of the whole molecule and has the following structure:

WSAP, were assigned (see Table 3 below) according to $^{13}$C NMR and $^1$H PMR spectra and two-dimensional COSY, TOCSY, ROESY, and HSQC spectra, and, on this basis, the structural formula of the polysaccharide portion of WSAP was drawn up.

FIG. 2. The WSAP typical $^1$H PMR-spectrum. The 3-5% solution of WSAP in $D_2O$ at 55° C. studied using Bruker DRX 600 MHz NMR Spectrometer (Germany) (trimethylsilyl propanoic acid, TMSP, was used as the internal standard); this spectrum was also used for drawing up the structural formula of WSAP.

FIG. 3. The structural formula of the polysaccharide portion of WSAP. Spectra were decoded using two-dimensional homonuclear COSY, TOCSY, and ROESY spectra and heteronuclear $^1$H/$^{13}$C HMQS spectrum, wherein m=3-5,

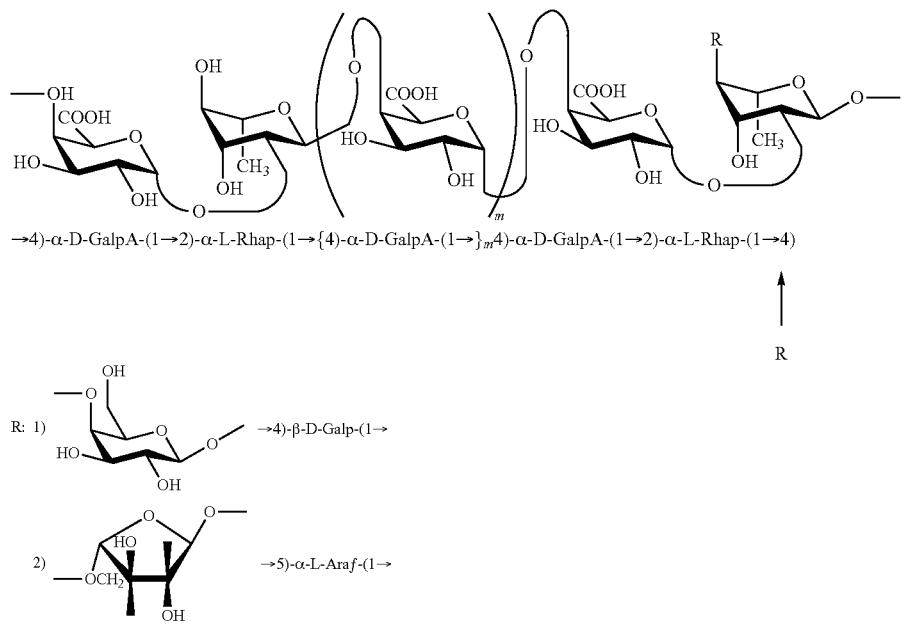

→4)-α-D-GalpA-(1→2)-α-L-Rhap-(1→{4)-α-D-GalpA-(1→}$_m$4)-α-D-GalpA-(1→2)-α-L-Rhap-(1→4)

R: 1) →4)-β-D-Galp-(1→

2) →5)-α-L-Araƒ-(1→ where m=3-5 and every second α-L-Rhap residue bears an R substituent, where R is the monosaccharide or oligosaccharide residues of β-D-galactopyranose, which in their turn bear monosaccharide or oligosaccharide residues of α-L-arabinofuranose, with ramnose to galacturonic acid weight ratio of 1:6 to 1:4.

The peptide portion of the molecule of acidic peptidoglycan is 4 to 20%. The lipid portion of the molecule is represented by fatty acids and is 2 to 7%. In this embodiment, the molecular weight of the substance is 500 kD to 17000 kD. A pharmaceutical composition has been formulated which exerts antimicrobial, antiviral, and immunomodulatory activities, particularly towards dendritic cells, and comprises the created active substance in effective amount and a pharmaceutically acceptable carrier or filler.

BRIEF DESCRIPTION OF THE DRAWINGS

FIG. 4A is a graph showing purity of sorted dendritic cells; FIG. 4B is a histogram showing CD80 expression; FIG. 4C is histogram showing CD86 expression; the black line indicates incubation with WSAP; the gray line indicates the control (incubation without WSAP); the dashed line indicates the isotype control for WSAP; and the dotted line indicates the isotype control for incubation without WSAP; and FIG. 4D—normalized data showing the increase of CD80 and CD86 expression under influence of WSAP. Normalized mean values and standard deviations based on the data of 3 experiments are shown (* significance P<0.05).

FIGS. 5A-5B are the graphs illustrating WSAP induced in vitro production of IL-6, MCP-1, and TNF-α cytokines by mouse macrophages, wherein: FIG. 5A is a graph showing TNF-α (1), and IL-6 (2); FIG. 5B is a graph showing MCP-1; X-axis: WSAP, μg/ml; Y-axis: cytokine concentration (pg/ml) in the culture medium; mean values and standard deviations based on the data of 3 experiments are shown.

FIGS. 7A-7B illustrate how WSAP increases CD86 and CD69 expression on human dendritic cells, wherein: FIG. 7A illustrates identification of myeloid dendritic cells (mDC) as $Lin1^{neg}CD11c^{high}CD123^{neg}HLA-DR^{high}$ using flow cytometry; FIG. 7B shows histograms of CD86 and CD69 expression on human myeloid dendritic cells (mDC).

DETAILED DESCRIPTION OF THE PREFERRED EMBODIMENTS

The proposed method of producing a plant-derived substance with high antimicrobial, antiviral, and immunostimulatory activities, particularly towards dendritic cells, consists in that the chopped potato sprouts used as plant raw materials are extracted with water, then the aqueous extract is centrifuged, a salt agent is added to the extract, and the resulting saline solution is then concentrated using ultrafiltration through a 300-kD filter, then the solution is frozen for 24 hours, thawed, and filtered, and the pellet thus obtained is removed, and the raw peptidoglycan is precipitated from the solution by using an acidic salt agent and is further treated with alkali, then the alkaline solution is dialyzed against distilled water on a 12-kD filter, and the peptidoglycan having a molecular weight of 500 kD to 17000 kD is purified from the resulting solution using gel permeation chromatography.

Sodium chloride is mainly used as a salt agent, and an inorganic ammonium salt is used as an acidic salt agent at the precipitation stage.

The present method differs from the known method (Russian Patent no. 2195308 A 61K 35/78) in several important stages of the process: (1) the concentration stage of the aqueous plant extract is performed in the salt solution, particularly NaCl-containing solution, using ultrafiltration through a 300-kD filter; (2) an additional stage of freezing of the solution obtained after ultrafiltration; and (3) the stage of precipitation is performed with the acidic salt agent; and (4) an additional stage of dialysis is applied prior to chromatographic purification.

The combination of specific features of the proposed method and execution of the above procedures made it possible to produce a novel substance with good yield, which is well soluble in water and has immunostimulatory activity, particularly towards dendritic cells, and strong antiviral and antimicrobial activities. The produced novel substance (its identified part) is a water-soluble acidic peptidoglycan (hereinafter WSAP) having a molecular weight of 500 kD to 17000 kD, which is a complex biopolymer comprising the polysaccharide, peptide, and lipid portions, where the polysaccharide portion is 40-60%, the peptide portion is 4% to 20%, and the lipid portion is 2% to 7% and contains fatty acids, mainly palmitic acid.

Figure 1:
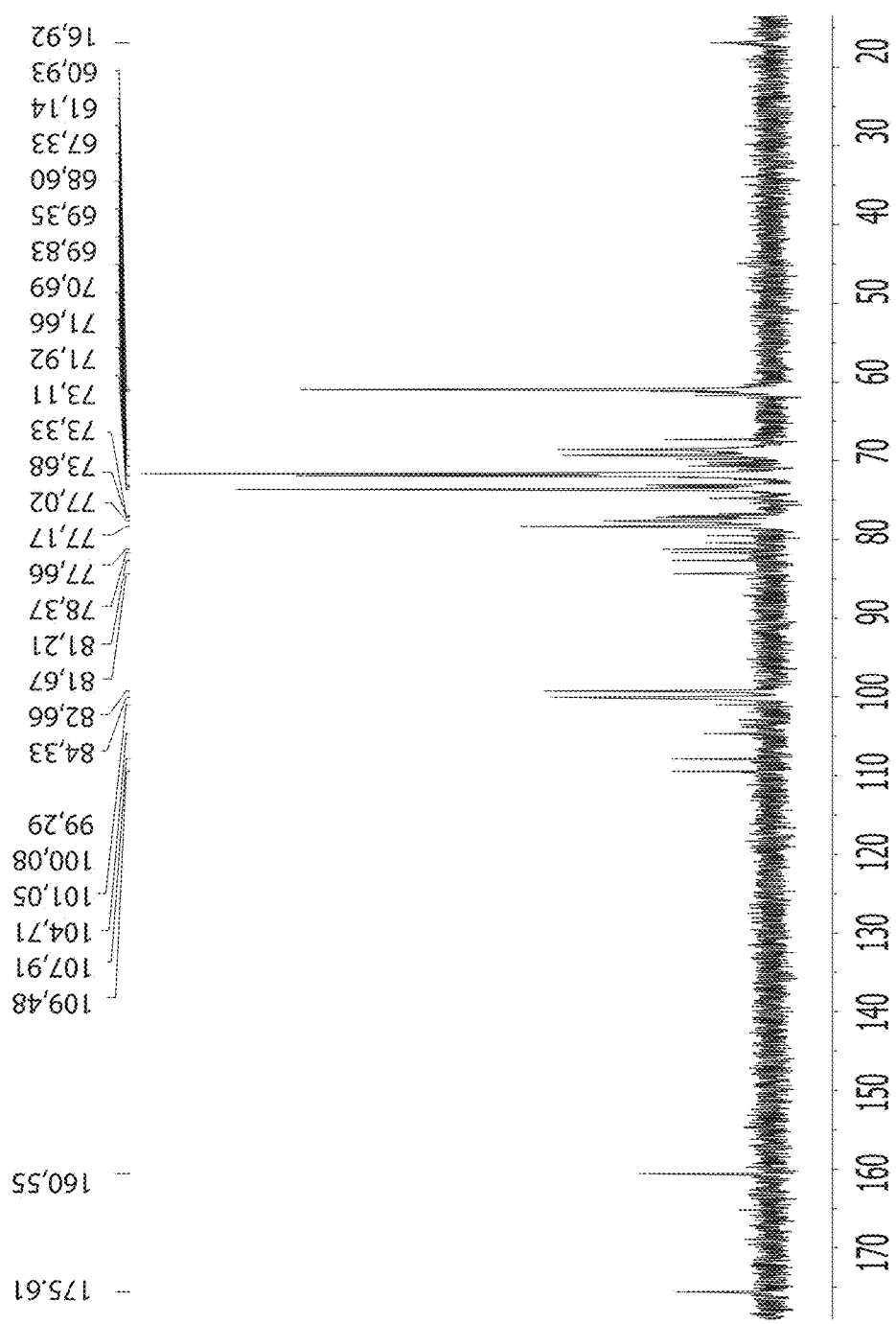
FIG. 1. WSAP typical $^{13}$C NMR-spectrum. The 3-5% solution of WSAP in $D_2O$ at 55° C. was studied using Bruker DRX 600 MHz NMR Spectrometer (Germany); chemical shifts of the polysaccharide portion of the molecule of water-soluble acidic peptidoglycan, hereinafter each second residue α-L-Rhap residue carries an R substituent, where R is the monosaccharide or oligosaccharide residues of β-D-galactopyranose, which in their turn bear monosaccharide or oligosaccharide residues of α-L-arabinofuranose, with ramnose to galacturonic acid weight ratio of 1:6 to 1:4.
Figure 2:
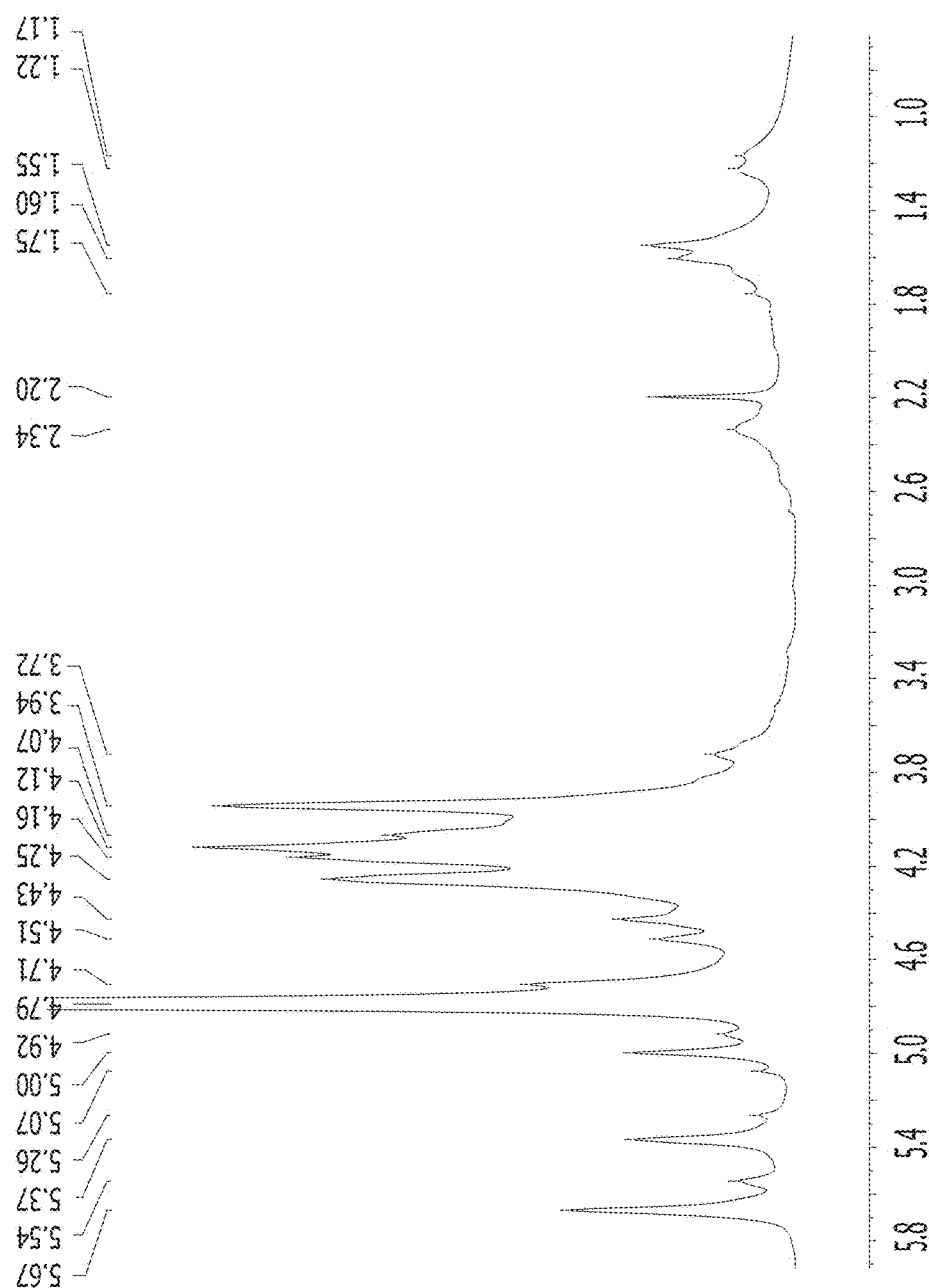
Figure 3:
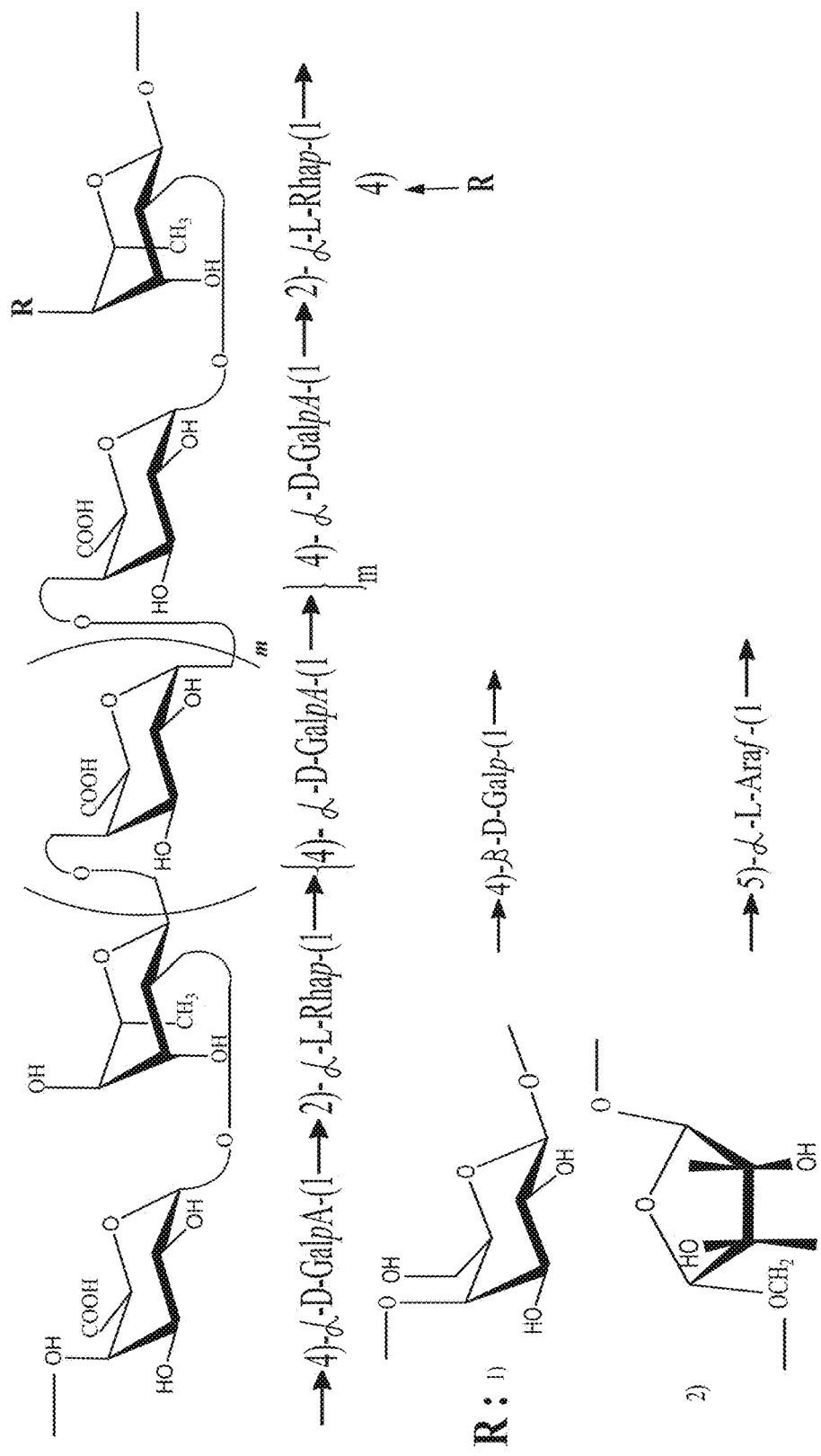
Figure 4A:
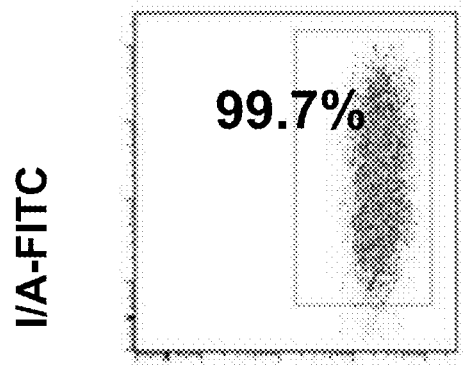
FIGS. 4A-4D illustrate the effect of WSAP on sorted murine splenic dendritic cells, wherein specifically.
Figure 4B:
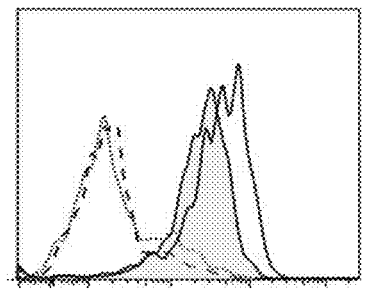
Figure 4C:
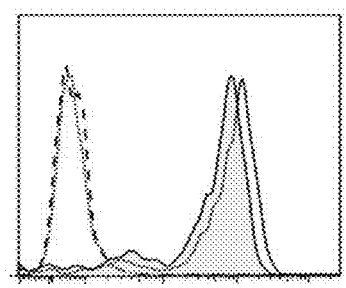
Figure 4D:
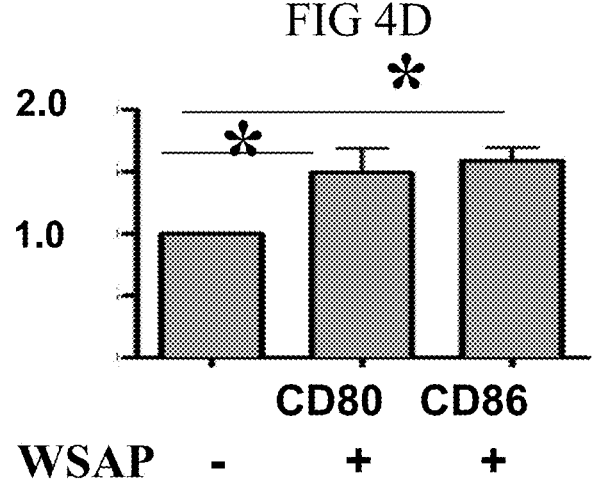

Based on the $^{13}$C NMR (typical $^{13}$C NMR spectrum, FIG. 1) and $^{1}$H PMR (typical $^{1}$H PMR spectrum, FIG. 2) spectroscopy and two-dimensional COSY, TOCSY, ROESY, and HSQC spectra, chemical shifts of the polysaccharide portion of the molecule of WSAP were assigned (Table 3) and the following structural formula of WSAP represented on FIG. 3 was drawn up:

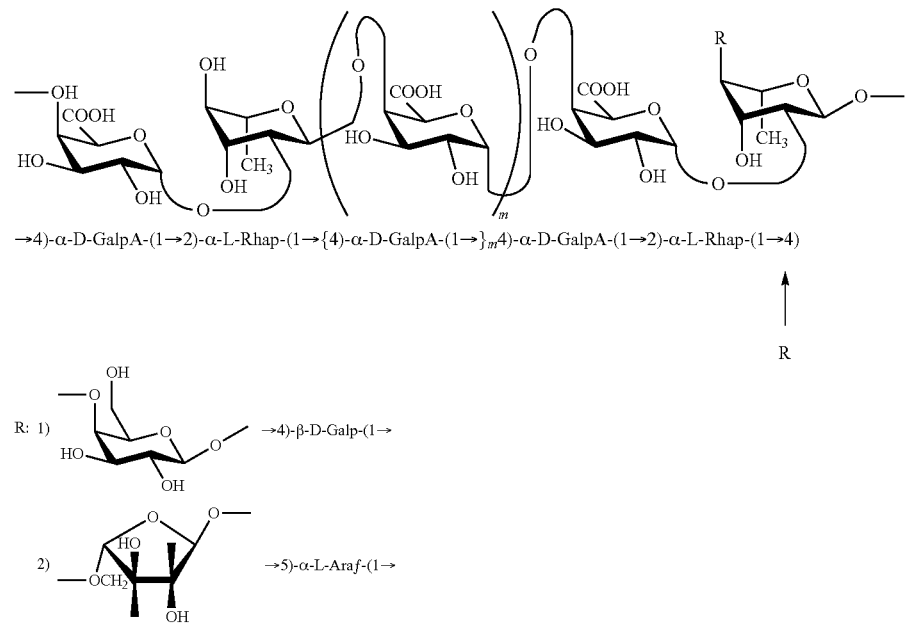

where m=3-5 and every second α-L-Rhap residue bears an R substituent.

where R is the monosaccharide or oligosaccharide residues of β-D-galactopyranose, which in their turn bear monosaccharide or oligosaccharide residues of α-L-arabinofuranose, with ramnose to galacturonic acid weight ratio of 1:6 to 1:4.

The stage of ultrafiltration of the salt solution (NaCl) of the aqueous extract through a 300 kD filter made it possible to eliminate non-covalent interactions between polymers and monomers of the aqueous extract and thereby more efficiently remove multiple impurities smaller than 300 kD and more efficiently purify polymeric substances with a molecular weight bigger than 300 kD.

The additional stage of freezing-thawing made it possible to purify the acidic peptidoglycan from non-active, poorly soluble polymers such as glucans, allowing to obtain a glucose-free peptidoglycan and thereby improve its purity, homogeneity and, as a consequence, its activity.

Precipitation of polymers was performed in one stage, without precipitation with alcohol, and an acidic inorganic ammonium salt was used as a salt agent. The proposed unconventional ultrafiltration at the concentration stage and the additional stage of freezing-thawing also made it possible to exclude precipitation with alcohol.

Precipitation with the acidic salt agent and removal of the precipitate after freezing-thawing made it possible to separate the raw acidic peptidoglycan from multiple satellite impurities such as polysaccharides, proteins, and other polymers with their molecular weight bigger than 300 kD.

After purification using gel-permeation column chromatography on TSK HW-75F or TSK HW-65F, the targeted product having a molecular weight of 500 kD to 17000 kD is collected.

The substance (WSAP) produced by this method, novel by its structural parts, is a complex biopolymer comprising the polysaccharide, peptide, and lipid portions and is different from the known acidic peptidoglycan (Russian Patent no. 2195308 A 61K 35/78, 27.12.2002), it has the following characteristics:

The polysaccharide portion does not contain glucose. The polysaccharide portion of the molecule comprises a galacturonic acid as the main monosaccharide, galactose, arabinose, and ramnose (see the structural formula in FIG. 3).

According to NMR spectra, the ramnose to galacturonic acid weight ratio is 1:6 to 1:4, while the same ratio for the known acidic peptidoglycan (Russian Patent no. 2195308 A 61K 35/78) is about 1:12 to 1:8.5.

2. The peptide portion of the molecule of WSAP is 4-20 wt %, while for the known acidic peptidoglycan (Russian Patent no. 2195308 A 61K 35/78) it was 13-+3%.

3. The lipid portion of the molecule consists of fatty acids. The amount of fatty acids in a sample, mainly palmitic acid (C-16), is 2% to 7%, while the known peptidoglycan (Russian Patent no. 2195308 A 61K 35/78) does not comprise the lipid portion.

In addition to the identified structural parts, the novel substance (WSAP) contains unknown, new chemical structural elements that make up the remaining percentage of the substance.

4. The novel substance (WSAP) produced by the above described method has immunostimulatory activity, particularly towards dendritic cells, and strong antimicrobial and antiviral activities. The substance has a good solubility in water, which makes it possible to create a pharmaceutical composition which is based on the claimed substance and includes pharmaceutically acceptable carriers or fillers taken in efficient amounts.

5. The method makes it possible to produce the targeted product with a good yield.

EXAMPLES OF HOW TO USE THE INVENTION

Example 1

Making the Target Product WSAP

Five kilograms of potato sprouts (batch 1) were chopped in 10 L of water and extracted for 2 hours at room temperature, with stirring. The mixture was squeezed using a mechanical press. 500 g of sodium chloride was added to the aqueous extract and dissolved, and the solution was concentrated to 1 L by ultrafiltration through a 300 kD filter.

The solution was frozen for 24 hours. After thawing and filtering, peptidoglycans were precipitated with an acidic salt agent, ammonium chloride. For this purpose, 1 L of saturated ammonium chloride solution was added to 1 L of the concentrate. The precipitate was pelleted by centrifugation, then 50 ml of distilled water was added to it, and 25% ammonia solution was added dropwise with stirring until the precipitate was completely dissolved. The solution was dialyzed using a 12 kD membrane against distilled water.

The resulting solution was introduced into a TSK HW-75F column. The column was eluted using distilled water. The high molecular peak having a molecular weight of 500 kD to 17000 kD was collected. The solution was concentrated on a rotor evaporator and freeze-dried. The yield of the desired product (WSAP) was 640 mg.

Acidic sugars were quantified by color reaction with 3,5-dimethylphenol in concentrated sulphuric acid (A. I. Usov, M. I. Bilan, N. G. Klochkova. —Botanica Marina, 1995, 38, 43-51). The acidic sugars content was 30.3%.

Neutral sugars were analyzed as polyol acetates by GLC (P. Albersheim. —Methods Enzymol., 1987, 118, 3-40). The neutral sugars content in WSAP was 26.9%.

Peptides were quantified by the Lowry method by using bovine serum albumin as a standard (O. H. Lowry, N. J. Rosenbrough et al., J. Biol. Chem., 1951, 193, 265-275). The peptide content in WSAP was 19.5%.

Fatty acids were determined using GLC as fatty acid methyl esters produced from polysaccharides by methanolysis in 1M HCl in methanol (at 100° C., 5 h). The lauric acid methyl ester (C12) was added as the internal standard. The fatty acid (mainly the palmitic acid (C16)) content in the sample was 7%.

Based on the PNR spectrum, the Rhap:GalpA ratio was calculated as 1:6 (chemical shift of 5.67 and 1.60).

The molecular weight analysis was performed using gel permeation chromatography: column, d=10 mm, L=500 mm; filler—Toyopearl HW75F; liquid phase—0.05% sodium azide in deionized water; elution rate=0.6 ml/min; and RI-detector Gilson 131. Calibration was performed using standard dextrans of 500 kD, 1500 kD, 3000 kD, and 17000 kD molecular weights (Polymer Standards Service GmbH, Germany). Under specified chromatographic conditions, the molecular weight of WSAP lies within the range of 500 kD to 17000 kD.

TABLE 1

The yield and composition of four batches WSAP produced from four batches of potato sprouts using the method described in this example.

|  | Batch 1 | Batch 2 | Batch 3 | Batch 4 |
|---|---|---|---|---|
| Yield, mg | 640 | 585 | 609 | 672 |
| Acidic sugars, % | 30.3 | 27.0 | 27.6 | 32.0 |
| Neutral sugars, % | 26.9 | 21.8 | 24.6 | 27.2 |
| Peptides, % | 19.5 | 13.8 | 8.3 | 17.6 |
| Fatty acids, % | 7.0 | 6.3 | 6.1 | 6.2 |
| Rhap:GalpA ratio | 1:4 | 1:6 | 1:4 | 1:5 |

Example 2

Producing of WSAP by Using an Acidic Salt Agent

This example is similar to Example 1 except that after thawing and filtration, WSAP is precipitated with an acidic salt agent, ammonium sulfate. The yield of the desired product is 560 mg. The acidic sugars content is 19.1%; the neural sugars content is 21.0%; the peptide content (by the Lowry method) is 4%; and the fatty acids content is 2.5%. Based on the PNR spectrum, the Rhap:GalpA ratio is calculated as 1:5 (chemical shift of 5.66 and 1.60).

The procedure of the targeted product obtaining was repeated using three more batches of potato sprouts.

TABLE 2

The yield and composition of four batches WSAP produced from four batches of potato sprouts using the method described in this example.

|  | Batch | Batch 2 | Batch 3 | Batch 4 |
|---|---|---|---|---|
| Yield, mg | 560 | 537 | 511 | 606 |
| Acidic sugars, % | 19.1 | 23.3 | 22.9 | 19.8 |
| Neutral sugars, % | 21.0 | 25.4 | 18.0 | 20.9 |
| Peptides, % | 4.0 | 7.5 | 4.8 | 13.0 |
| Fatty acids, % | 2.5 | 5.9 | 3.0 | 7.9 |
| Rhap:GalpA ratio | 1:5 | 1:6 | 1:4 | 1:5 |

Example 3

Structural Analysis of the Polysaccharide Portion of WASP

The $^{13}$C NMR spectra of 3-5% WASP solutions in $D_2O$ were measured at 55° C. using a Bruker DRX 600 MHz NMR Spectrometer (TMSP, was used as the internal standard). Two-dimensional COSY, TOCSY, ROESY, and HSQC spectra were measured using standard Bruker methods.

Chemical shifts were assigned in accordance with reference data (Advances in carbohydrate chemistry and biochemistry, vol. 42, 1984, p. 193-225) and recent literature data on NMR spectroscopy of polysaccharides.

Based on 13C NMR (typical 13C NMR spectrum, FIG. 1) and 1H PMR (typical 1H PMR spectrum, FIG. 2) spectroscopy and two-dimensional COSY, TOCSY, ROESY, and HSQC spectra, chemical shifts of the polysaccharide portion of WSAP molecule were assigned (Table 3).

TABLE 3

Chemical shifts of fragments of the polysaccharide portion of WASP molecule.

Chemical shift of $^{13}$C ($\delta_c$ acetone 31.45 ppm) and $^1$H ($\delta_H$ TSP 0.0 ppm)

| Residue | C-1 H-1 | C-2 H-2 | C-3 H-3 | C-4 H-4 | C-5 H-5 | C-6 |
|---|---|---|---|---|---|---|
| →4)-α-D-GalpA- (1→ | 101.0$^a$ 99.5$^b$ 5.38$^a$ 4.98$^b$ | 72.8 3.65 | 72.6 3.85 | 77.9 3.96 | 74.5 3.97 | 176.6 |
| →2)-α-L-Rhap- (1→ | 101.0 5.34 | 78.3 4.02 | 70.4 3.95 | 72.9 3.44 | 70.8 3.66 | 17.9 1.27 |
| →2)-α-L-Rhap- (1→ 4 ↑ | | | | | | 18.0$^c$ 1.31$^c$ |
| →4)-β-D-Galp- (1→4 | 105.5 104.2 4.63 4.52 | 73.0 3.70 3.68 | 74.6 3.78 | 78.8 4.18 | 75.8 3.72 | 62.0 3.88, 3.83 |
| α-L-Araf-(1→ | 110.3 5.26 | 82.0 4.13 | 78.2 4.02 | 85.4 4.15 | 62.4 3.84 3.73 | |

TABLE 3-continued

Chemical shifts of fragments of the polysaccharide portion of WASP molecule.

| Residue | Chemical shift of $^{13}C$ ($\delta_c$ acetone 31.45 ppm) and $^{1}H$ ($\delta_H$ TSP 0.0 ppm) | | | | | |
|---|---|---|---|---|---|---|
| | C-1 H-1 | C-2 H-2 | C-3 H-3 | C-4 H-4 | C-5 H-5 | C-6 |
| →5)α-L-Araf-(1→ | 108.9 510 | 82.0 4.13 | 78.2 4.02 | 82.2 4.23 | 68.4 3.90 3.80 | |

[a]For the residue glycosylating α-D-GalpA at the C-4 hydroxyl
[b]For the residue glycosylating α-L-Rhap at the C-2 hydroxyl
[c]2,4-di-subsituted residue
WSAP has the polysaccharide portion of the following structure (FIG. 3):

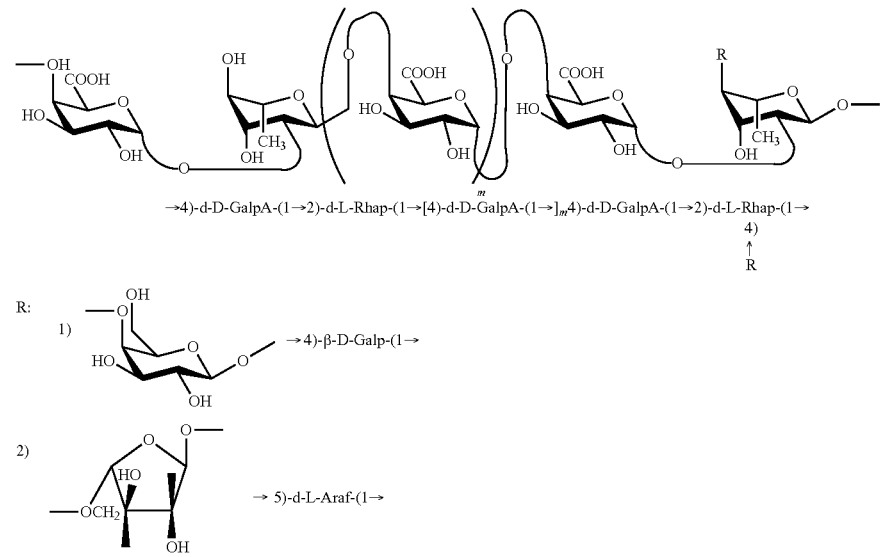

→4)-d-D-GalpA-(1→2)-d-L-Rhap-(1→[4)-d-D-GalpA-(1→]$_m$4)-d-D-GalpA-(1→2)-d-L-Rhap-(1→
4)
↑
R R:
1) →4)-β-D-Galp-(1→
2) →5)-d-L-Araf-(1→ where m=3-5 and every second α-L-Rhap residue bears an R substituent, where R is the monosaccharide or oligosaccharide residues of β-D-galactopyranose, which in their turn bear monosaccharide or oligosaccharide residues of α-L-arabinofuranose, with ramnose to galacturonic acid weight ratio of 1:6 to 1:4.

Example 4

WSAP has the Immunostimulatory Effect on Dendritic Cells Isolated from Mouse Spleen BALB/c female mice of 18-20 g body weight from Stolbovaya breeding nursery were used in the experiments. Mice were euthanized with $CO_2$ in a chamber. Mouse spleens were aseptically removed and minced; splenic mononuclear cells were isolated on Ficoll 1.09 g/cm$^3$ (1500 rpm at 15° C. for 25 min) and then were washed two times by centrifugation (1200 rpm at 4° C. for 10 min) in the phosphate buffered saline (10 mM $Na_2HPO_4$, 137 mM NaCl, and 2.7 mM KCl) supplemented with 0.5% BSA, 1% glucose, and 10 mM HEPES, pH 7.3-7.5 (complete PBS). The isolated splenic mononuclear cells were re-suspended in the complete PBS, stained with a mixture of anti-CD19 FITC, anti-I-A PE, and anti-CD11c PerCP-Cy5-5 antibodies (BD Biosciences) for 20 min at 4° C., washed with the complete PBS, and re-suspended in the same solution at a concentration of 20-30 million cells/ml. Dendritic cells were sorted on a BD FACSAria™ II Cell Sorter (BD Biosciences) using a marker combination CD19$^-$, CD11c$^+$, I-A$^+$. The purity of the sorted dendritic cells was 97-99% (FIG. 4). The isolated dendritic cells were suspended in a complete culture medium (RPMI-1640 supplemented with 10% fetal calf serum (FCS), 2 mM L-glutamine, nonessential amino acids, 1 mM sodium pyruvate, 50 μM β-mercaptoethanol, 100 U/ml penicillin, and 100 U/ml streptomycin) at a concentration of 10$^5$ cells per 1 ml and were transferred to a 96-well plate at 20,000 cells per well in 200 μl of medium in duplets.

WSAP was added at a concentration of 10 μg/ml to the test cultures of dendritic cells. The corresponding volume of physiological saline solution was added to the control cultures of dendritic cells. Cells were incubated for 20 hours (37° C., 5% $CO_2$). After the end of incubation, the content of wells was washed out with a complete PBS, transferred to centrifuge microtubes, and centrifuged at 1200 rpm for 8 min. A mixture of anti-CD80 FITC and anti-CD86 APC antibodies was added to the pellet, incubated for 20 min at 4° C., washed with a complete PBS, and the cells were re-suspended in 200 µl of the same solution with the addition of 2 µg/ml DAPI. CD80 and CD86 expression on dendritic cells was analyzed using a BD FACSAria™ II Cell Sorter (BD Biosciences). The findings (Table 4) show that the expression of CD80 and CD86 costimulatory molecules, which are required for presenting antigens to T cells and further activation of T cells, is significantly ($p<0.05$) increased on dendritic cell surface under the influence of WSAP.

TABLE 4

An increased expression of CD80 and CD86 costimulatory molecules on mouse dendritic cells under the influence of WSAP.

| Binding of fluorescent antibody on dendritic cell surface | CD80 and CD86 expression (fluorescence normalized by the control sample) | | |
|---|---|---|---|
| | Mean | Standard deviation | Significance |
| CD80-FITC | 1.5 | 0.12 | P < 0.05 |
| CD86-APC | 1.6 | 0.1 | P < 0.05 |

Note:
Data are means and standard deviations for three samples, which are normalized by the corresponding means for three control samples. The control samples of dendritic cells were incubated in a complete culture medium without any stimulatory ligands.

Example 5

WSAP Activates the Expression of CD86 Costimulatory Molecule, Production of IL-12, IL-6, MCP-1, and TNF-α cytokines, and NO Production by Mouse Bone Marrow Derived Dendritic Cells and Macrophages Increased expression of CD86 molecule on the mouse dendritic cell surface under the influence of WASP BALB/c female mice of 18-20 g body weight from Stolbovaya breeding nursery were used in the experiments. Mice were euthanized with $CO_2$ in a chamber. The femoral bone marrow was aseptically washed out using a G25 syringe and a complete PBS, The cells were suspended in a complete PBS and pelleted by centrifugation at 1200 rpm for 10 min, erythrocytes were lysed by hypotonic shock by adding 9 ml of sterile distilled water for 15 s, and erythrocyte lysis was stopped by adding 1 ml of 10× Hank's balanced salt solution and then 20 ml of a complete PBS solution. The cells were pelleted and suspended in the complete PBS. Cell concentration and viability were assessed by flow cytometry using calibrated beads and propidium iodide (2 µg/ml) on a BD FACSAriar™ II Cell Sorter (BD Biosciences).

10 million bone marrow cells in 10 ml of a complete culture medium (DMEM supplemented with 10% FCS, 2 mM L-glutamine, nonessential amino acids, 1 mM sodium pyruvate, 50 µM β-mercaptoethanol, 100 U/ml penicillin, and 100 U/ml streptomycin) supplemented with 10 ng/ml GM-CSF (GIBCO) were cultured in 90-mm Petri dishes for 9 days. The medium (supplemented with GM-CSF) was changed on days 3 and 6 after the onset of culture. On day 9, the nonadherent cell fraction was collected from the culture, pelleted by centrifugation (at 1200 rpm for 10 min), and suspended in the complete PBS, and the cell concentration and viability was assessed by flow cytometry using calibrated beads and propidium iodide (2 µg/ml) on a BD FACSAria™ II Cell Sorter (BD Biosciences). Dendritic cells were identified by flow cytometry using CD11c and MHC class II expression on cell surface. The dendritic cell content in the used suspensions was 70-80%.

Dendritic cells at a concentration of 1 million cells per 1 ml of the complete DMEM culture medium were transferred into wells of a 24-well cell culture plate (Nunclon). WSAP was added at a concentration of 10 µg/ml into three wells. Three other wells with dendritic cells without any effectors served as negative controls. Eighteen hours after incubation at 37° C. and 5% $CO_2$, the cells were transferred to centrifuge tubes, the content of wells was washed out with the complete PBS and was transferred to the same tubes, and the cells were pelleted by centrifugation at 1200 rpm for 10 min. The cell pellet was stained with a mixture of anti-CD11c-PE and anti-CD86-APC (BD Biosciences) monoclonal antibodies labeled with fluorochromes, and cells were analyzed by flow cytometry using a BD FACSAria™ II Cell Sorter (BD Biosciences). The results (Table 5) show that under the influence of WSAP mouse dendritic cells increase 5.9-fold the expression of CD86 costimulatory molecules, which are required for antigen-presenting function of these cells and activation of T cells.

TABLE 5

An increased expression of CD86 costimulatory molecules on mouse dendritic cells under the influence of WSAP.

| Medium in which dendritic cells were cultured | CD86 expression, relative fluorescence units | | |
|---|---|---|---|
| | Mean | Standard deviation | Significance |
| Complete culture medium | 4295.1 | 2132 | — |
| Complete culture medium with WSAP (10 µg/ml) | 25176.5 | 3423 | P < 0.001 |

Note:
Data are means and standard deviations for three identical cultures

Increased production of IL-12 cytokine in mouse dendritic cells under the influence of WSAP Bone marrow derived dendritic cells were obtained by culturing bone marrow cells in the presence of 10 ng/ml GM-CSF for 9 days, as is described above in this example. Two million cells per 1 ml of a complete culture medium were cultured in wells of a 24-well cell culture plate (Nunclon). WSAP (10 µg) was added into two wells, and the corresponding volume of physiological saline was transferred to another two wells that served as negative controls. The plate was incubated for 18 hours in a $CO_2$ incubator, then brefeldin-A was added at a final concentration of 5 µM, and the plate was incubated for another 6 hours.

After the end of incubation, 2 ml of cold complete PBS was added into each well, gently pipetted, and transferred to 4.5-ml tubes (BD Biosciences). Cells were pelleted by centrifugation (for 10 min at 1200 rpm), then the cell pellet was resuspended in 1 ml of complete PBS and transferred to 1.2-ml microtubes. The cells were pelleted by centrifugation (for 10 min at 1200 rpm). A mixture of anti-I-A FITC and anti-CD11c PerCP-Cy5-5 antibodies (BD Biosciences) was added to 50 µl of the cell pellet and incubated for 20 min in the darkness at 4° C., then cells were washed with a complete PBS. The pellet was shaken and mixed with 100 µl of FixPerm solution (BD Biosciences), incubated for 20 min, and then washed twice with a PermWash solution (BD Biosciences). The cell pellet was suspended in 50 µl of PermWash, divided into two aliquots of 20 µl each, to which anti-IL-12 PE antibody (BD Biosciences) was added, and incubated for 30 min. The cells were washed twice with PermWash solution, suspended in 200 μl of complete PBS, and analyzed by flow cytometry on a BD FACSAria™ II Cell Sorter (BD Biosciences). Data presented in Table 6 show that the production of IL-12 cytokine is significantly increased in dendritic cells under the influence of WSAP, specifically, the number of cells synthesizing IL-12 is increased 4.3-fold (p<0.01).

Table 6. An increased production of IL-12 by mouse dendritic cells under the influence of WSAP.

TABLE 6

An increased production of IL-12 by mouse dendritic cells under the influence of WSAP.

| Medium in which dendritic cells were cultured | Percentage of dendritic cells producing IL-12 | | |
|---|---|---|---|
| | Mean | Standard deviation | Significance |
| Complete culture medium | 2.7 | 1.1 | — |
| Complete culture medium supplemented with WSAP (10 μg/ml) | 11.7 | 1.0 | P < 0.01 |

Increased secretion of IL-6, MCP-1, and TNF-α cytokines and NO production by macrophages under influence of WSAP Mouse bone marrow derived macrophages were obtained by the incubation of bone marrow in the presence of 10 ng/ml GM-CSF for 9 days, as is described above in this example. On day 9, the fraction of adherent cells was collected from the culture, pelleted by centrifugation (at 1200 rpm for 10 min), and suspended in a complete PBS, and the cell concentration and viability was assessed by flow cytometry using calibrated beads and propidium iodide (2 μg/ml) on a BD FACSAria™ II Cell Sorter (BD Biosciences). Macrophages at a concentration of 1 million cells per 1 ml of a complete DMEM culture medium were transferred into wells of a 24-well tissue culture plate (Nunclon). WSAP was added at a concentration of 10 μg/ml, 1 μg/ml, or 0.1 μg/ml in triplets. The corresponding volume of physiological saline was added into three wells that served as negative controls. The plate was incubated for 24 hours at 5% $CO_2$ and 37° C. After the end of incubation, samples of culture supernatants were collected to determine a concentration of cytokines and NO. Concentrations of TNF-α, IL-6, and MCP-1 cytokines were measured on a BD FACS Aria™ II Cell Sorter (BD Biosciences) using a BD™ Cytometric Bead Array, Mouse Inflammation Kit (BD Biosciences) according to the manufacture's instructions. Cytokine concentration was calculated using FCAP Array™ Software v1 (BD Biosciences).

Figure 5A:
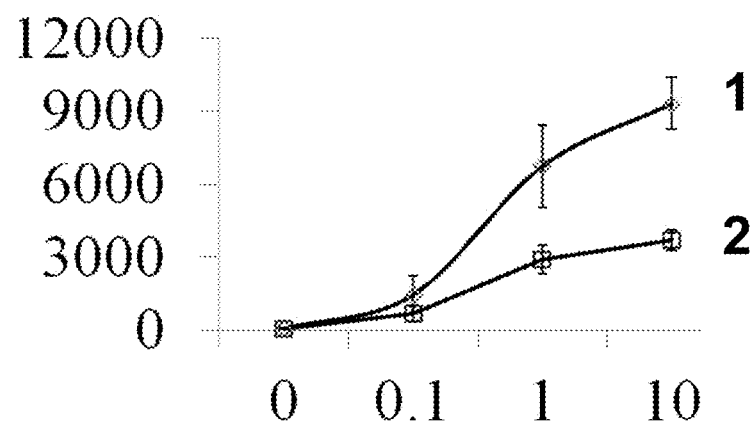
Figure 5B:
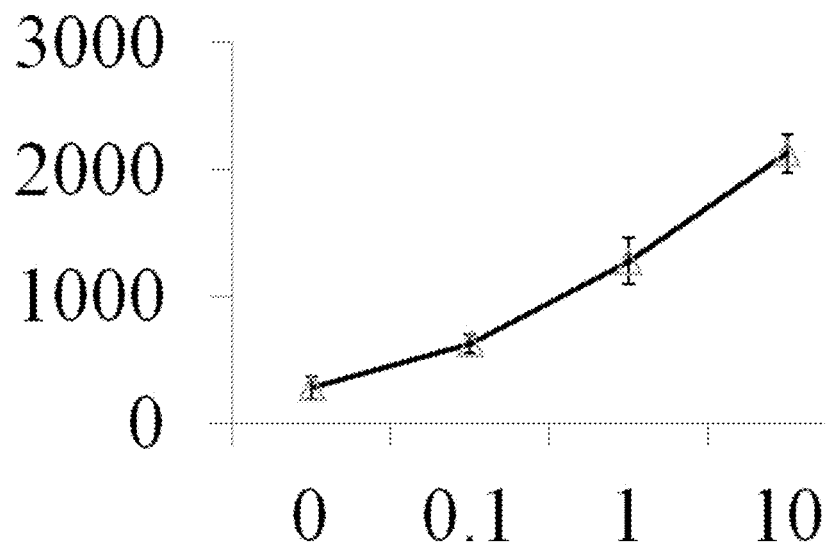

As is shown in FIG. 5, WSAP significantly simulates the production of TNF-α, IL-6, and MCP-1 cytokines. More specifically, concentration of IL-6, MCP-1, and TNF-α in the culture supernatant was increased 186-fold, 8-fold, and 54-fold, respectively, under influence of WSAP.

The NO production was assessed by measuring of sodium nitrite in the culture supernatant using the Griess reaction (L. C. Green, 1982). The Griess reagent was prepared immediately before the assay by mixing equal volumes of solution A (0.1% naphthyl ethylenediamine dihydrochloride solution in water) and solution B (1% sulfanilamide in 5% H3PO4). To determine the concentration of sodium nitrite, the culture fluid (50 μl) was added to wells of a 96-well flat-bottom plate (Medpolymer), and 150 μl of Griess reagent was added to each well. The reaction mixture was incubated for 10 min at room temperature, and the optical density was measured using a Dynex MRX spectrophotometer at $\lambda=545$ nm. The reaction mixture containing an equivalent volume of a complete cell culture medium instead of culture supernatant was used as a control. Two-fold dilutions of NaNO2 in the complete cell culture medium were used as standard samples to obtain the calibration curve.

Figure 6:
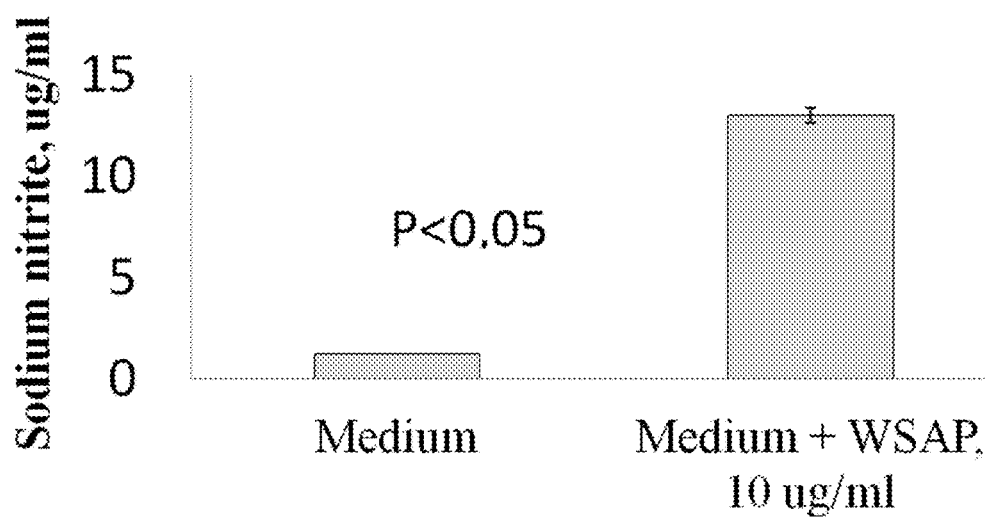
FIG. 6. WSAP induces nitrogen oxide (NO) production in murine macrophages in vitro.

The findings show that macrophages actively produce NO under the influence of WSAP. Based on the data in FIG. 6, we may conclude that the NO production is stimulated ten-fold by WSAP.

Example 6

WSAP Activates Expression of CD69 and CD86 on Human Dendritic Cells

Whole blood from healthy donors was collected into Vacutainer tubes (Becton-Dickinson) containing heparin, diluted 1:1 with RPMI-1640 medium, and incubated for 18 hours in the presence of 5 μg/ml WSAP. After the end of incubation, blood samples were stained with a mixture of antibodies against Lin1-FITC (CD3, CD14, CD16, CD19, CD20, CD56), CD123 PE, HLA-DR APC-H7, CD11c BD Horizon, CD69 APC, and CD86 PerCP Cy5.5. (BD Biosciences) for 20 min, then 1 ml of BD FACS Lysing Solution (BD Biosciences) was added for removing erythrocytes and fixing white blood cells. Samples were analyzed by flow cytometry on a BD FACS Aria II Cell Sorter.

Figure 7A:
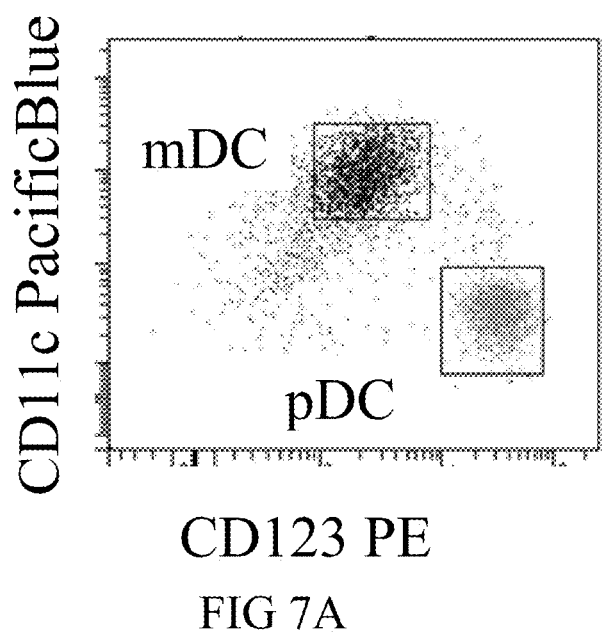
Figure 7B:
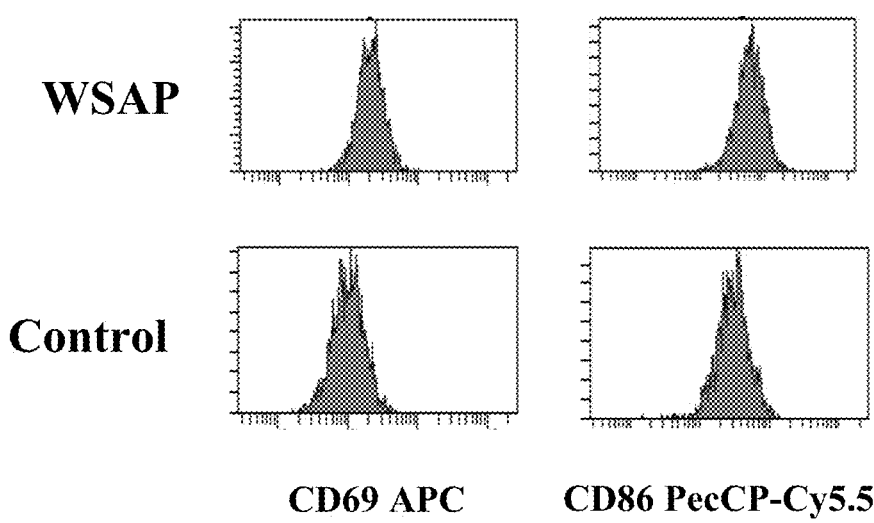

Data obtained (Tables 7 and 8, and FIG. 7) show that the expression of CD86 costimulatory molecule (p<0.05) and CD69 activation molecule (p<0.05) is increased 2-fold on human myeloid dendritic cells under the influence of WASP.

TABLE 7

An increased expression of CD86 costimulatory molecule on human dendritic cells under the influence of WASP.

| Medium in which dendritic cells were cultured | CD86 expression, relative fluorescence unit | | |
|---|---|---|---|
| | Mean | Standard deviation | Significance |
| Complete culture medium | 3425 | 1005 | — |
| Complete culture medium supplemented with WSAP (5 μg/ml) | 6686 | 666 | P < 0.05 |

TABLE 8

An increased expression of CD69 activation molecule on human dendritic cells under the influence of WSAP.

| Medium in which dendritic cells were cultured | CD69 expression, relative fluorescence unit | | |
|---|---|---|---|
| | Mean | Standard deviation | Significance |
| Complete culture medium | 1137 | 378 | — |

TABLE 8-continued

An increased expression of CD69 activation molecule on
human dendritic cells under the influence of WSAP.

| Medium in which dendritic cells were cultured | CD69 expression, relative fluorescence unit | | Significance |
|---|---|---|---|
| | Mean | Standard deviation | |
| Complete culture medium supplemented with WSAP (5 µg/ml) | 2230 | 367 | P < 0.05 |

Example 8

A Pharmaceutical Composition of WSAP Stimulates Cytokine Production In Vivo (CBA×C57Bl/6)F1 male mice of 18-20 g body weight from Stolbovaya breeding nursery were used in the experiments. A pharmaceutical composition was created by mixing a dry, lyophilized preparation of WSAP and a pharmaceutical isotonic solution of sodium chloride, filtered through a 0.22 µm filter, and injected intraperitoneally at a dose of 10 µg in 0.2 ml per mouse. Mice injected with 0.2 ml of the pharmaceutical grade isotonic solution of sodium chloride were used as controls. All groups comprised five mice. Mice were euthanized at 1, 3, and 6 hours. Right before injection of the above solutions, mice were used as time point "0 h". To obtain peritoneal exudate, the 3 ml volume of cold isotonic (0.9% sodium chloride) solution was injected intraperitoneally. Samples of collected peritoneal exudate were centrifuged at 1500 rpm for 10 min to remove cells, and the supernatant was assayed for the cytokine concentration. The concentration of cytokines IL-6 and MCP-1 was measured using a BD™ Cytometric Bead Array, Mouse inflammation Kit (BD Biosciences) on a BD FACSAria™ ii Cell Sorter (BD Biosciences) according to the manufacturer's instructions. Cytokine concentration was calculated using FCAP Array™ Software v1 (BD Biosciences).

Figure 8:
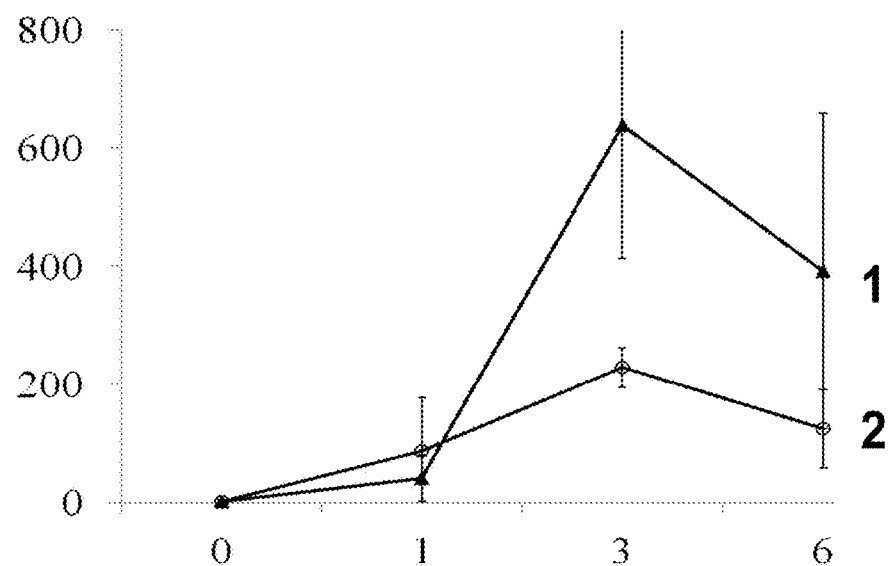
FIG. 8. A pharmaceutical composition of WSAP in an isotonic solution of sodium chloride induces the production of MCP-1 (1) and IL-6 (2) cytokines in mice; WSAP (10 ug/mouse) was injected intraperitoneally as a volume of 0.2 ml; cytokines were measured in the peritoneal wash harvested 1-6 hrs after injection of WASP; X-axis: hours after administration of the WSAP; Y-axis: cytokine concentration (pg/ml); data are means and standard deviations for three mice at each time point.

Data obtained show that the parenterally injected pharmaceutical composition of WSAP and isotonic sodium chloride solution caused a significant stimulation of IL-6 and MCP-1 production in mice, with the peak values of 220 pg/ml and 600 pg/ml, respectively, 4 hours after the injection (see FIG. 8).

Example 9

WSAP has an Antimicrobial Activity

The enhancement of antimicrobial defense in animals with a pharmaceutical composition containing WSAP in effective amount and pharmaceutical NaCl was studied using a model of purulent bacterial abscess in guinea pigs. The pharmaceutical composition was prepared by dissolving of the 5 µg WSAP sterile lyophilizate in 1 ml of the pharmaceutical grade isotonic NaCl solution designed for injectable use. Experimental purulent wounds in laboratory guinea pigs (100-150 g body weight) were made as follows. During the experiment, not only the condition of experimental purulent wound but also the general condition of animals and their mobility and appetite were monitored.

Animals were divided into two groups, the main group and the control group, each comprising 10 animals. To create an experimental wound abscess, the animals were shaved in the interscapular region under general (ketamine+relanium) anesthesia. Then a skin area of 2 cm² was dissected, with the subcutaneous fat left intact. The soft tissue of the wound bed and borders was squeezed with Kocher's forceps for 3-4 min. One milliliter of bacterial suspension containing $2 \times 10^9$ microbial bodies of Staphylococcus aureus (strain 150) and Eseherichia coli (strain 20), most common infectious agents of surgical wounds, was injected under the squeezed soft tissue. Two to three days after inoculation, the treatment and monitoring of purulent wound inflammation was started.

Standard procedures for local purulent wounds routinely used in clinical surgical practice were applied during the treatment of animals from the control and the test groups. Three days after infectioning of the wounds, necrotizing soft tissue was aseptically removed (necrectomy). The skin surrounding the wound was disinfected with a 3% iodine solution, and the wound itself was washed with 3% hydrogen peroxide solution. Then a gauze dressing with Levomecol ointment was applied to the wound surface. Wound dressings were changed every day.

The animals from the main group were injected intramuscularly with 5 µg of WSAP on days 1, 3, and 5 of treatment. The animals from the control group were injected intramuscularly with 1 ml of 0.9% NaCl.

Monitoring of the wound process in animals of the control and the test groups showed a significant acceleration of healing of purulent wounds in animals that were injected with WSAP. Two days after infectioning of the wounds, in all the animals, irrespective of treatment option, adynamia, motor atonia, increased water intake, and decreased solid food intake, i.e., general symptoms of serious, purulent inflammation were observed along with the local symptoms of purulent process. Locally, the wound was covered with a scab raised above the swollen and red areas surrounding the wound. On pressing the scab, pus began to ooze from the wound. The scab could be easily removed, without bleeding. After removing the scab, soft tissue appeared to be swollen and partly necrotic, filled with pus and fibrin clots. Three days after the onset of treatment, the animals of the main group were more mobile than those of the control group. The animals of both groups ate little but their water intake was increased. Local edema and hyperemia around the wound were slightly decreased. The wound bed was covered with a layer of pus and fibrin. In the animals treated with WSAP, edema and redness of wound edges were less pronounced. No significant differences between the test and the control groups could be obtained using planimetry of wound areas. Five days after the onset of treatment, the animals injected with WASP showed improved mobility and appetite and decreased edema and hyperemia of tissues surrounding the wound. Islands of pink granulations sprang up at the bottom of the wound in 7 of 10 animals of the test group and in 4 of 10 animals of the control group (differences between the groups were significant, p<0.05). The wound area was reduced twice in both groups, as compared to the initial area, and no significant differences in the wound area were observed on this day between the groups. Seven days after the onset of treatment, the animals of the main group were active, their appetite was completely restored, and water intake was slightly higher than that of the healthy animals. Locally, the wound surface was completely cleared, and the wound bed was covered with a layer of pale pink granulations in most animals. The wound area was reduced to 31% of the initial wound area. In the control group, the wound surface was also cleared and covered with a layer of granulation tissue, but the wounds produced a large amount of serous, mucous exudate. There was no edema or hyperemia of skin around the wound. The wound area was 38% of the initial wound area and was significantly larger (p<0.05) than that in the test group. On day 9 of treatment, in the animals treated with WSAP, wounds were filled with pink granulation tissue and the wound area was reduced to 13% of the initial wound area, while in the control group, the wound area was reduced to 18% of the initial wound area (p<0.05). At the same time, the wound surface was covered with dirty-gray fibrin coating and bleeded on touch in half of the animals of the control group. Fifteen days after the onset of treatment, wounds were almost completely epithelized in the animals treated with WSAP. In the control group, wounds were completely epithelized two days later, i.e., 17 days after the onset of treatment.

Overall, the comparison of dynamic changes in purulent wound infection caused by *St. aureus* and *E. coli* showed that the intramuscular injection of 5 μg of WSAP led to more rapid clearance of infection in the wound, enhanced granulation tissue formation and epithelization, and complete healing of the wound.

Example 10

Study of the Antiviral Activity of WSAP in the In Vitro Cytomegalovirus Infection Model The reference strain of Cytomegalovirus (CMV, strain AD 169) was used in this study. The CMV infection activity was estimated using highly sensitive cells, human embryonic diploid lung fibroblasts (HELF) obtained from the collection of tissue cultures of Ivanovsky Institute of Virology, Ministry of Health of the Russian Federation. HELF cells were cultured using the DMEM culture medium supplemented with 10% FCS, 2 mM L-glutamine, and 50 μg/ml of gentamicin. Preliminary study of WSAP in vitro cytotoxicity showed that WSAP at doses of 3000 μg/ml, 300 μg/ml, 30 μg/ml, 3 μg/ml, and 0.3 μg/ml had no cytotoxic effects on HELF cells within seven days of exposure.

To estimate the antiviral (anti-CMV) activity of WSAP, HELF cells monolayers in 48-well plates (2×105 cell/ml) were covered with the serum-free medium containing the test substance at its different concentrations (final concentration of 300 μg/ml, 30 μg/ml, 3 μg/ml, and 0.3 μg/ml) and incubated for 1 hour. Then, the HELF cell monolayer was infected with CMV at a multiplicity of infection of 10-4 PFU/cell during 1 hour at 37° C. The cell monolayer was washed, and a complete culture medium was added. Cells were incubated at 370 C in 5% CO2 for 5 days. Cells infected with the same dose of CMV but not treated with the test substance were used as the control. Each concentration of the WSAP was studied in triplets.

The number of CMV-infected plaques was estimated by immunoperoxidase technique using monoclonal antibodies to CMV proteins. The dose of WSAP inhibiting CMV was determined according to the ratio (percent) of the number of infected cells (plaques) in the test culture previously treated with the WSAP to the number of plaques in the culture of control, untreated cells. Then the concentration of WSAP corresponding to the 50% inhibition of CMV plaque formation (inhibitory dose, ID50) was calculated using Probit Analysis package (version 1.0, by A. Polekhin).

Figure 9:
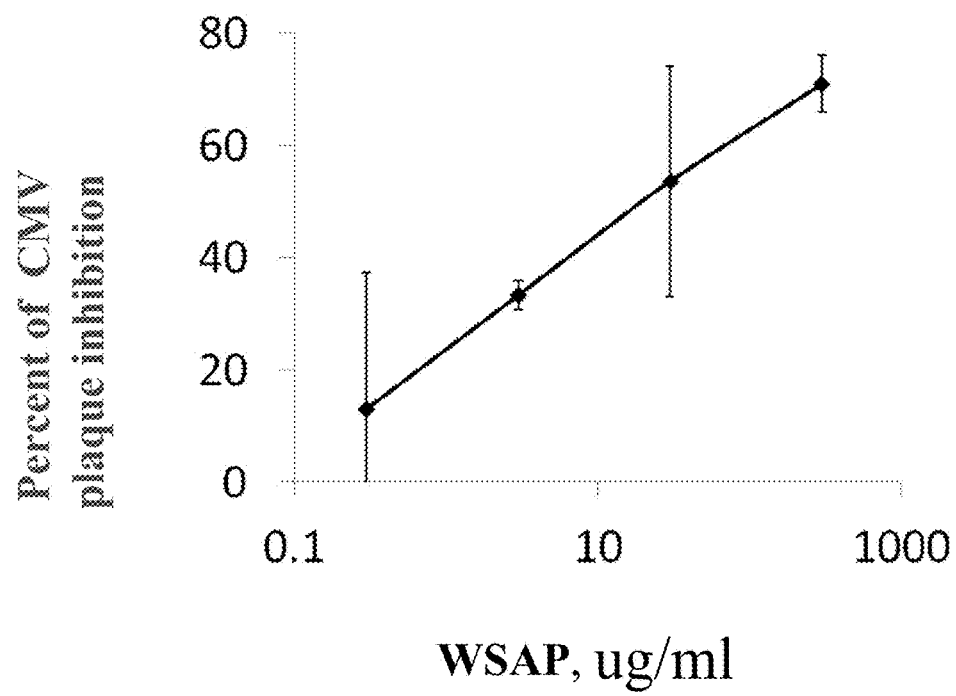
FIG. 9. Antiviral activity of WSAP against cytomegalovirus (CMV). Human embryonic lung fibroblasts (HELF, $2\times10^5$ cell/ml) were incubated for 5 days in the presence of CMV ($10^{-4}$ PFU/cell) and different concentrations of WSAP; the number of CMV-infected plaques was calculated by the immunoperoxidase technique using monoclonal antibodies specific to CMV-proteins; the inhibiting effect was calculated as a ratio of the number of infected cells (plaques) in the test culture preliminarily treated with the test substance to the number of plaques in the untreated control cell culture.

The WSAP at a dose of 300 μg/ml, 30 μg/ml, and 3 μg/ml inhibited plaque formation by 63.3%, 41/1%, and 16.7%, respectively, relative to the control (FIG. 9), The ID50 was calculated to be 18 μg/ml (95% interval 8-48 μg/ml).

One can conclude that WSAP is nontoxic to HELF cells and has an antiviral effect against CMV infection.

Examples 1-10 presented above prove that a novel substance has been obtained, which is a water-soluble acidic peptidoglycan (WSAP) having a molecular weight of 500 kD to 17000 kD and comprising polysaccharide, peptide, and lipid portions. Based on $^{13}$C NMR и $^{1}$H PMR spectroscopy, the structure of the polysaccharide portion was decoded. The substance obtained using the proposed method is a novel substance and has the following specific features:

The polysaccharide portion of WSAP does not contain glucose. The polysaccharide portion of the molecule contains a galacturonic acid as the main monosaccharide, galactose, arabinose, and ramnose. According to NMR spectroscopy, the weight ratio between ramnose and galacturonic acid is 1:6 to 1:4.

The peptide portion of WSAP is 4-20 wt %.

The lipid portion of the molecule is 2-7% and consists of fatty acids, mainly palmitic acid.

The above presented biological tests (FIGS. 4-8) prove that WSAP, a novel substance obtained using the proposed method, has immunostimulatory activity towards dendritic cells and macrophages and strong antimicrobial and antiviral activities. The substance has a good solubility in water, which makes it possible to create a pharmaceutical composition using pharmaceutically acceptable carriers or fillers taken in sufficient amounts.

Thus, the task of the present invention, namely to produce a novel plant-derived polysaccharide-based substance from available plant raw materials and with good yield, which is well soluble in water and has not only strong antiviral and antimicrobial activities but also immunostimulatory activity, particularly towards dendritic cells, develop the effective and technological method of producing the said substance, and create a pharmaceutical composition based on the said substance and having a high pharmacological effect has been solved.

INDUSTRIAL APPLICABILITY

The present invention complies with the industrial applicability criterion. All chemical operations are adapted to industrial conditions of production and purification of a novel biologically active polymer.

What is claimed is:

1. A pharmaceutical composition comprising a substance and a pharmaceutically acceptable carrier or filler, wherein the substance has antimicrobial and antiviral activities, and immunostimulatory activities towards dendritic cells, and wherein the substance comprises:

(i) 40-60% (w/w) polysaccharide, wherein the polysaccharide comprises the following structure:

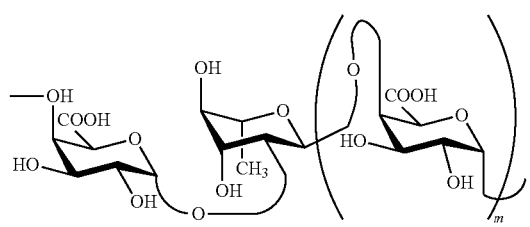

-continued

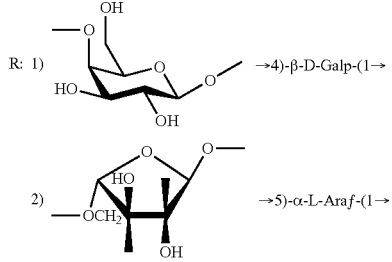

→4)-α-D-GalpA-(1→2)-α-L-Rhap-(1→{4)-α-D-GalpA-(1→}$_m$4)-α-D-GalpA-(1→2)-α-L-Rhap-(1→4)

wherein m=3-5 and every second α-L-Rhap residue bears an R substituent,

R is a monosaccharide or an oligosaccharide comprising β-D-galactopyranose and optionally comprising α-L-arabinofuranose and the polysaccharide portion comprises a weight ratio of rhamnose to galacturonic acid of 1:6 to 1:4;

(ii) 4-20% (w/w) peptide; and (iii) 2-7% (w/w) lipid.

2. The pharmaceutical composition of claim 1, wherein the molecular weight of the substance is 500 kDa to 17,000 kDa.

3. The pharmaceutical composition of claim 1, wherein the polysaccharide does not comprise glucose.

4. The pharmaceutical composition of claim 1, wherein the substance is isolated from plant materials from a plant of the Solanaceae family.

5. The pharmaceutical composition of claim 1, wherein the substance is isolated from potato sprouts.

6. The pharmaceutical composition of claim 1, wherein R is an oligosaccharide comprising β-D-galactopyranose and α-L-arabinofuranose.

* * * * *